US009474843B2

(12) United States Patent
Li et al.

(10) Patent No.: US 9,474,843 B2
(45) Date of Patent: Oct. 25, 2016

(54) FLUID-STORING, FILTERING, AND GAS-DISCHARGING APPARATUS AND HEMATOMA EVACUATOR BASED ON THE LIQUID-STROING, FILTERING, AND AIR-DISCHARGING APPARATUS

(71) Applicants: Guangcheng Li, Qingdao (CN); Na Lu, Qindao (CN); Wen Li, Qindao (CN); Wenyong Zhang, Qindao (CN)

(72) Inventors: Guangcheng Li, Qingdao (CN); Na Lu, Qindao (CN); Wen Li, Qindao (CN); Wenyong Zhang, Qindao (CN)

(73) Assignee: Guangcheng Li, Qingdao, Shandong (CN)

( * ) Notice: Subject to any disclaimer, the term of this patent is extended or adjusted under 35 U.S.C. 154(b) by 109 days.

(21) Appl. No.: 14/354,927

(22) PCT Filed: Oct. 9, 2012

(86) PCT No.: PCT/CN2012/082638
§ 371 (c)(1),
(2) Date: Apr. 28, 2014

(87) PCT Pub. No.: WO2013/064005
PCT Pub. Date: May 10, 2013

(65) Prior Publication Data
US 2014/0303579 A1    Oct. 9, 2014

(30) Foreign Application Priority Data

Oct. 29, 2011    (CN) .......................... 2011 1 0336365

(51) Int. Cl.
*A61M 1/00*      (2006.01)
*A61M 27/00*     (2006.01)
(Continued)

(52) U.S. Cl.
CPC .............. *A61M 1/34* (2013.01); *A61M 1/0056* (2013.01); *A61M 1/3627* (2013.01); *A61M 1/3626* (2013.01); *A61M 2205/7545* (2013.01); *B01D 19/00* (2013.01); *B01D 19/0031* (2013.01)

(58) Field of Classification Search
CPC .. A61M 1/3627; A61M 1/34; A61M 1/0056; A61M 2205/7545; A61M 2202/0028; A61M 1/0023; A61M 1/0025; A61M 1/02; A61M 1/0066; A61M 1/0281; A61M 1/36; A61M 1/3621; A61M 1/3626; A61M 1/3632; A61M 1/3653; A61M 1/1658; A61M 1/3633; A61M 1/3635; A61M 1/3636; A61M 1/3638; A61M 2206/10; A61M 2206/11; A61M 2206/20; A61M 2206/22; A61B 17/320016; A61B 17/32002; A61B 2017/320024; A61B 2017/320032; A61B 17/3205; A61B 17/320758; A61B 17/320725; A61B 17/32075; A61B 17/320783; A61B 2017/320775; A61F 9/00763
See application file for complete search history.

(56) References Cited

U.S. PATENT DOCUMENTS 3,939,078 A * 2/1976 Servas ............... B01D 19/0031
                                                     210/436
4,320,001 A * 3/1982 Le Boeuf ............... B01D 35/00
                                                     210/120
(Continued)

*Primary Examiner* — Adam Marcetich
(74) *Attorney, Agent, or Firm* — Raymond Y. Chan; David and Raymond Patent Firm

(57) ABSTRACT

A fluid-storing, filtering, and gas-discharging apparatus (2) comprising a fluid holder (21), a gas detector (23), and a filter (22). The fluid holder (21) has a protruding apex structure and comprises a fluid inlet and a fluid outlet. A gas-discharging pipe in communication with the outside is arranged on the protruding apex of the fluid holder (21). The gas detector (23) is arranged on the gas-discharging pipe. The filter (22) is fixed within the fluid holder (21) and is connected to the fluid outlet. The fluid-storing, filtering, and gas-discharging apparatus (2) uses the fluid holder (21) and the filter (22) to implement the storage and filtration of a working fluid, while at the same time, the fluid holder (21) having the protruding apex structure ensures complete discharging of gases mixed in the working fluid, thus achieves the goals of fluid storage, filtration, and gas discharge, and provides great reliability.

7 Claims, 2 Drawing Sheets

(51) Int. Cl.
  *A61M 1/34*   (2006.01)
  *B01D 19/00*   (2006.01)
  *A61M 1/36*   (2006.01)

(56) References Cited

U.S. PATENT DOCUMENTS

| | | | | |
|---|---|---|---|---|
| 4,344,777 | A * | 8/1982 | Siposs | A61M 1/3627 |
| | | | | 210/436 |
| 4,690,762 | A * | 9/1987 | Katsura | B01D 19/0031 |
| | | | | 210/436 |
| 4,932,987 | A * | 6/1990 | Molina | B01D 19/0031 |
| | | | | 210/304 |
| 5,000,764 | A * | 3/1991 | Oshiyama | A61M 1/3627 |
| | | | | 210/188 |
| 5,188,588 | A * | 2/1993 | Schoendorfer | A61M 1/30 |
| | | | | 604/6.07 |
| 6,117,342 | A * | 9/2000 | Schnell | A61M 1/3627 |
| | | | | 210/188 |
| 7,108,785 | B1 * | 9/2006 | Plechinger | B01D 19/0031 |
| | | | | 210/188 |
| 2002/0114731 | A1 * | 8/2002 | Stringer | A61M 1/3626 |
| | | | | 422/44 |
| 2003/0040694 | A1 * | 2/2003 | Dorros | A61B 17/12109 |
| | | | | 604/8 |
| 2005/0192525 | A1 * | 9/2005 | Wieting | A61M 1/3627 |
| | | | | 604/6.09 |
| 2007/0021774 | A1 * | 1/2007 | Hogendijk | A61B 17/32075 |
| | | | | 606/200 |
| 2007/0055282 | A1 * | 3/2007 | Muschler | A61B 10/0233 |
| | | | | 606/92 |
| 2008/0281343 | A1 * | 11/2008 | Dewey | A61B 17/1675 |
| | | | | 606/180 |
| 2009/0084721 | A1 * | 4/2009 | Yardimci | A61M 1/1658 |
| | | | | 210/188 |
| 2011/0092875 | A1 * | 4/2011 | Beck | A61M 1/3627 |
| | | | | 604/6.09 |
| 2013/0018301 | A1 * | 1/2013 | Weaver | A61M 1/3627 |
| | | | | 604/28 |

* cited by examiner

FLUID-STORING, FILTERING, AND GAS-DISCHARGING APPARATUS AND HEMATOMA EVACUATOR BASED ON THE LIQUID-STROING, FILTERING, AND AIR-DISCHARGING APPARATUS

TECHNICAL FIELD

The present invention relates to the technical field of medical equipment and, in particular, to a fluid-storing, filtering, and gas-discharging apparatus for clinical application and a hematoma evacuator based on the fluid-storing, filtering, and gas-discharging apparatus.

BACKGROUND ART

The fluid suctioned from human body needs to be stored, filtered and gas-discharged before it is injected back into the body to achieve the purpose of curing diseases during the treatments of certain diseases. For example, intracranial hematoma aspiration is used in the present treatment of cerebral hemorrhage, and the hematoma is aspirated after being cut and pulverized by an aspirator in this technique. The aspirator is connected to a balance lavage device under the continuous negative pressure at the same time. The pulverized and aspirated hematoma is filtered and then injected back into the skull to remain the volume of hematoma cavity unchanged for the purpose of removing hematoma.

A patent application entitled "A Hematoma Evacuator" has been applied by the applicant on Apr. 25, 2010. In technology of the patent, filter and gas-discharging apparatuses are configured in separated configurations to store, filter and gas-discharge the sucked working fluid. Such design may however cause gas retention in the filter easily, which gas within the hematoma evacuator cannot be discharged by the gas-discharging apparatus and thereby may increase operation risk.

CONTENTS OF INVENTION

The present invention provides a fluid-storing, filtering, and gas-discharging apparatus, which can store and filter working fluid when it flows through and ensure that the gas mixed in the working fluid can be discharged, which is extremely suitable for the field of medical equipment with a great reliability.

Technical solutions to support the present invention are described as follows:

A fluid-storing, filtering, and gas-discharging apparatus comprises a fluid holder, a gas detector and a filter; the fluid holder has a protruding apex structure and comprises a fluid inlet and a fluid outlet; a gas-discharging pipe in communication with the outside is arranged on the protruding apex of the fluid holder, the gas detector is arranged on the gas-discharging pipe, and the filter is fixed within the fluid holder and is connected to the fluid outlet.

Ulteriorly, for the fluid-storing, filtering, and gas-discharging apparatus mentioned above, a baffle plate is arranged on the lower part of the fluid holder to divide the fluid holder into two fluid chambers which upper parts are connected. The fluid inlet is arranged at the top of the first fluid chamber and the filter is arranged in the second fluid chamber.

Preferably, the lower part of the fluid holder has a convex polyhedron structure in order to ensure that the fluid holder has certain compressive strength, so that its deformation can be reduced as much as possible.

Preferably, the upper part of the fluid holder has a tapered protruding apex structure in order to ensure that the gas in the fluid holder can be successfully discharged from the gas-discharging pipe disposed on its top.

The present invention provides a hematoma evacuator based on the fluid-storing, filtering, and gas-discharging apparatus. It can solve the problem that the gas within the hematoma evacuator cannot be completely discharged in the prior art, improve the reliability of the hematoma evacuator, and reduce the risk of hematoma clearance operation.

Technical solutions to support the present invention are described as follows:

A hematoma evacuator based on the fluid-storing, filtering, and gas-discharging apparatus consists of an aspirator configured with a rotor and a stator, a negative pressure aspirating device, and a rotating device connected to the aspirator respectively, wherein the negative pressure aspirating device comprises a fluid-storing, filtering, and gas-discharging apparatus and a circulating pump; the fluid-storing, filtering, and gas-discharging apparatus comprises a fluid holder, a gas detector, and a filter; the fluid holder has a protruding apex structure and comprises a fluid inlet and a fluid outlet; a gas-discharging pipe in communication with the outside is arranged on the protruding apex of the fluid holder, the gas detector is arranged on the gas-discharging pipe, and the filter is fixed within the fluid holder and is connected to the fluid outlet; the aspirator is connected to the fluid inlet of the fluid-storing, filtering, and gas-discharging apparatus; the fluid outlet of the fluid-storing, filtering, and gas-discharging apparatus is connected to the circulating pump; the circulating pump is connected to the aspirator to form a closed-loop pathway; the closed-loop pathway is filled with working fluid; and the circulating pump and the rotating device are both controlled by the electrical control unit.

Ulteriorly, for the hematoma evacuator based on the fluid-storing, filtering, and gas-discharging apparatus mentioned above, the pressure sensors are arranged on both the connecting pipes between the fluid-storing, filtering, and gas-discharging apparatus and the internal cavity of the stator of the aspirator and between the circulating pump and the internal cavity of the rotor of the aspirator, which aims to detect the pressure on the pipes at any time and ensure that the pressure within the system keeps a balanced state. The pressure sensors can detect whether the pressure within the pipes is in a predetermined range at all times. Meanwhile the pressure sensors are all controlled by the electrical control unit, which can monitor changes from the pressure sensors at any time so as to control the working state of the motor and the circulating pump at any time.

Furthermore, the hematoma evacuator based on the fluid-storing, filtering, and gas-discharging apparatus mentioned above can also be used to clean the hematoma if there is hematoma in a patient's bladder in clinical practice. A gasbag fixture is sleeved on the outer wall of the stator to fix the aspirator because it is not easy to fix an aspirator when operating on a bladder. The gasbag fixture comprises a gasbag, an inflation pipe and an inflation valve. The gasbag is filled with air after the aspirator is put into the bladder, so that the aspirator can be fixed by the gasbag and then the clearing operation can be performed. The aspirator can also be made into a flexible structure for adapting the body cavities, so a variety of uses of the present utility model can be achieved.

ADVANTAGEOUS EFFECTS

The fluid-storing, filtering, and gas-discharging apparatus mentioned in the present invention can store and filter the working fluid with the fluid holder and the filter and, at the same time, the fluid holder having the protruding apex structure can ensure complete discharging of gas mixed in the working fluid so as to achieve the goals of fluid-store, filtration, and gas-discharge with great reliability.

Secondly, the hematoma evacuator based on the fluid-storing, filtering, and gas-discharging apparatus mentioned in the present invention can make the gas mixed in the working fluid diffuse to the top of the fluid holder and then discharge the gas from the gas-discharging pipe arranged on the top by using the fluid-storing, filtering, and gas-discharging apparatus having a protruding apex structure to substitute the existing filter and the existing discharging and capacity-reducing appliance, so as to solve the problem that the gas in the hematoma evacuator cannot be completely discharged in the prior art, to improve the reliability of the hematoma evacuator, and, therefore, to reduce the risk of hematoma clearance operation.

1. aspirator; 11. rotor; 111. helical blade; 112. fluid inlet pole; 113. fluid spurting pole; 114. light source; 115. camera lens; 116. pressure sensor; 12. stator; 121. fluid suction pole; 13. stereotactic device; 2. fluid-storing, filtering, and gas-discharging apparatus; 21. fluid holder; 22. filter; 23. gas detector; 3. circulating pump; 4. electrical control unit; 5. rotating device; 6. pressure sensor; 7. pressure sensor; 8. gasbag fixture; 81. gasbag; 82. inflation pipe; 83. inflation presser;

The direction of the arrow in the figures represents the direction of the fluid flow.

SPECIFIC EMBODIMENTS

The present invention will be further described in detail with reference to the following drawings and specific embodiments.

Figure 1:
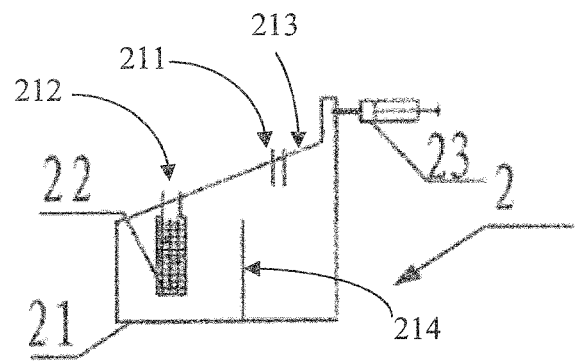
FIG. 1 shows a structure diagram of a fluid-storing, filtering, and gas-discharging apparatus of the present invention.

As shown in FIG. 1, the fluid-storing, filtering, and gas-discharging apparatus 2 mentioned in the present invention comprises a fluid holder 21, a filter 22, and a gas detector 23; the fluid holder 21 has a protruding apex structure and comprises a fluid inlet 211 and a fluid outlet 212; a gas-discharging pipe in communication with the outside is arranged on the protruding apex 213 of the fluid holder; the gas detector 23 is arranged on the gas-discharging pipe, and the filter 22 is fixed within the fluid holder and is connected to the fluid outlet 212.

The lower part of the fluid holder has a convex polyhedron structure in order to ensure that the fluid holder has certain compressive strength, so that its deformation can be reduced as much as possible. The upper part of the fluid holder has a tapered protruding apex structure in order to ensure that the gas in the fluid holder can be successfully discharged from the gas-discharging pipe disposed on its top.

Embodiment 1

A hematoma evacuator based on the fluid-storing, filtering, and gas-discharging apparatus comprises an aspirator 1 configured with a rotor 11 and a stator 12 and a negative pressure aspirating device and a rotating device 6 which are connected to the aspirator 1, wherein the negative pressure aspirating device comprises a fluid-storing, filtering, and gas-discharging apparatus 2 and a circulating pump 3; the fluid-storing, filtering, and gas-discharging apparatus comprises a fluid holder 21, a filter 22 and a gas detector 23; the fluid holder 21 has a protruding apex structure and comprises a fluid inlet 211 and a fluid outlet 212; a gas-discharging pipe in communication with the outside is arranged on the protruding apex 213 of the fluid holder 21; the gas detector 23 is arranged on the gas-discharging pipe; the filter 22 is fixed within the fluid holder 21 and is connected to the fluid outlet 212; the aspirator 1 is connected to the fluid inlet 211 of the fluid-storing, filtering, and gas-discharging apparatus 2; the fluid outlet 212 of the fluid-storing, filtering, and gas-discharging apparatus 2 is connected to the circulating pump 3; the circulating pump is connected to the aspirator 1 to form a closed-loop pathway; the circulating pump and the rotating device are both controlled by the electrical control unit 4.

In the present invention, the process of performing the clearance operation by the hematoma evacuator of the present invention will be described in detail by the example of the intracranial hematoma lump cleaning.

Figure 2:
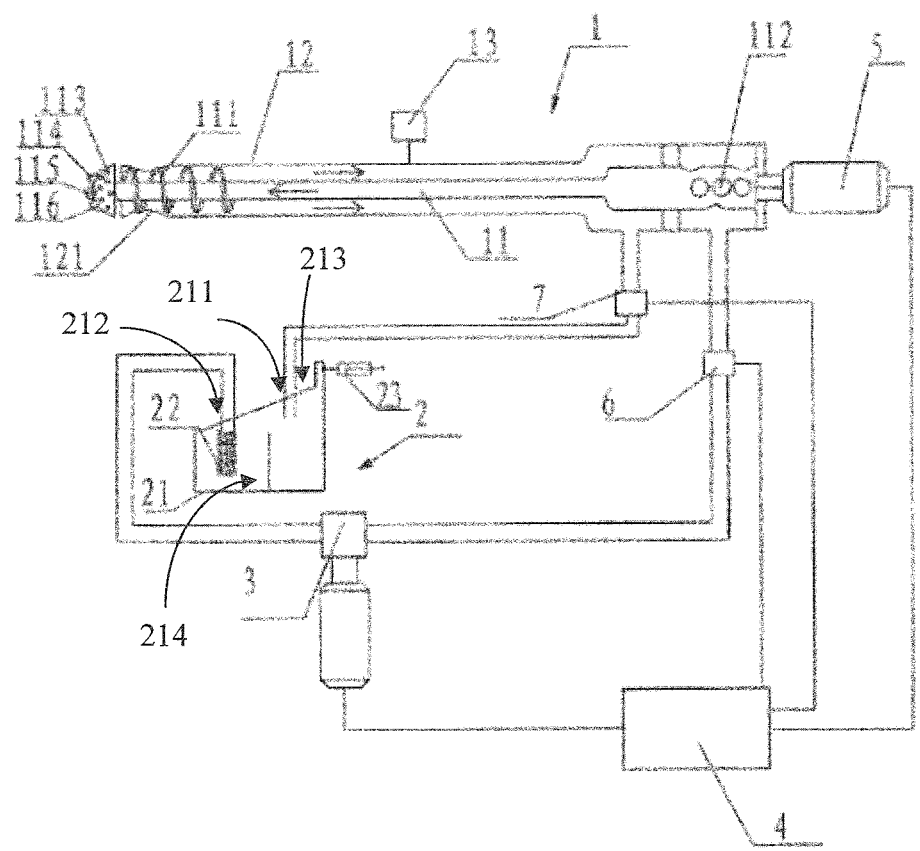
FIG. 2 shows a structure diagram of a hematoma evacuator based on the fluid-storing, filtering, and gas-discharging apparatus in the Embodiment 1 of the present invention.

Based on the fluid-storing, filtering, and gas-discharging apparatus shown in FIG. 2, the inside of the hematoma evacuator was filled with working fluid before use, and the hemolysis drug, such as urokinase, was added into the working fluid; as the electrical control unit 4 is started, the rotating device 5 and the circulating pump 3 will be started at the same time; insert the front of the aspirator 1 into the intracranial hematoma cavity, and the rotating device 5 drives the rotor 11 to rotate; the intracranial hematoma lump is aspirated into the fluid suction pole 121 of the stator 12 while it is pulverized by the helical blade 111 on the rotor 11; the system under the action of the circulating pump 3 comes to the negative pressure; the pulverized hematoma lump is aspirated into the internal cavity of the stator 12 of the aspirator, and then the pulverized hematoma lump is suctioned out by the pipes and enters the fluid holder 21 via the fluid inlet 211; by this time the hematoma lump within the working fluid precipitates to the bottom of the fluid holder 21, while the gas mixed within the working fluid will spill to the top of the fluid holder 21 and be discharged by the gas-discharging pipe; the hematoma lump mixed in the working fluid is further filtered by the filter 22; the filtered working fluid is spurted into the internal cavity of the rotor 11 again through the fluid outlet 212 by the circulating pump 3; that is, the working fluid is synchronously injected into cranial internal cavity by the rotor 11 of the aspirator to keep balance of the pressure in the cranial internal cavity. Meanwhile, the gas detector 23 arranged on the gas-discharging pipe will send out a signal when the gas discharges from the gas-discharging pipe, so that the medical staff can take relevant measures, e.g. stop operation to check whether the hematoma evacuator was working well to thereby reduce the risk of the operation.

A baffle plate 214 is arranged on the lower part of the fluid holder to divide the fluid holder into two fluid chambers, and the upper part of two fluid chambers is connected. The fluid inlet 211 is arranged at the top of the first fluid chamber, and the filter is arranged in the second fluid chamber. The working fluid from the fluid inlet 211 enters the first fluid chamber at first, and most of the hematoma lump in the working fluid precipitates in the first fluid chamber at this moment. Meanwhile the working fluid enters the second fluid chamber via the first fluid chamber as the upper parts of the fluid chambers are connected, and the fluid is discharged via the fluid outlet 212 after being filtered by the filter 22 within the second fluid chamber; this can more effectively prevent the hematoma lump being adsorbed on the filter, so that the reliability of the filter can be ensured.

The pressure sensor 7 is arranged on the connecting pipes between the fluid-storing, filtering, and gas-discharging apparatus 2 and the internal cavity of the stator 12 of the aspirator 1; the pressure sensor 6 is arranged on the connecting pipes between the circulating pump 3 and the internal cavity of the stator 11 of the aspirator; the pressure sensors 6 and 7 can detect whether the pressure within the pipes is in a predetermined range at all times and ensure that the pressure within the system keeps in a balanced state. The pressure sensors 6 and 7 are both controlled by the electrical control unit 4 that monitors changes from the pressure sensors at any time so as to control the working state of the motor and the circulating pump anytime.

Embodiment 2

Figure 3:
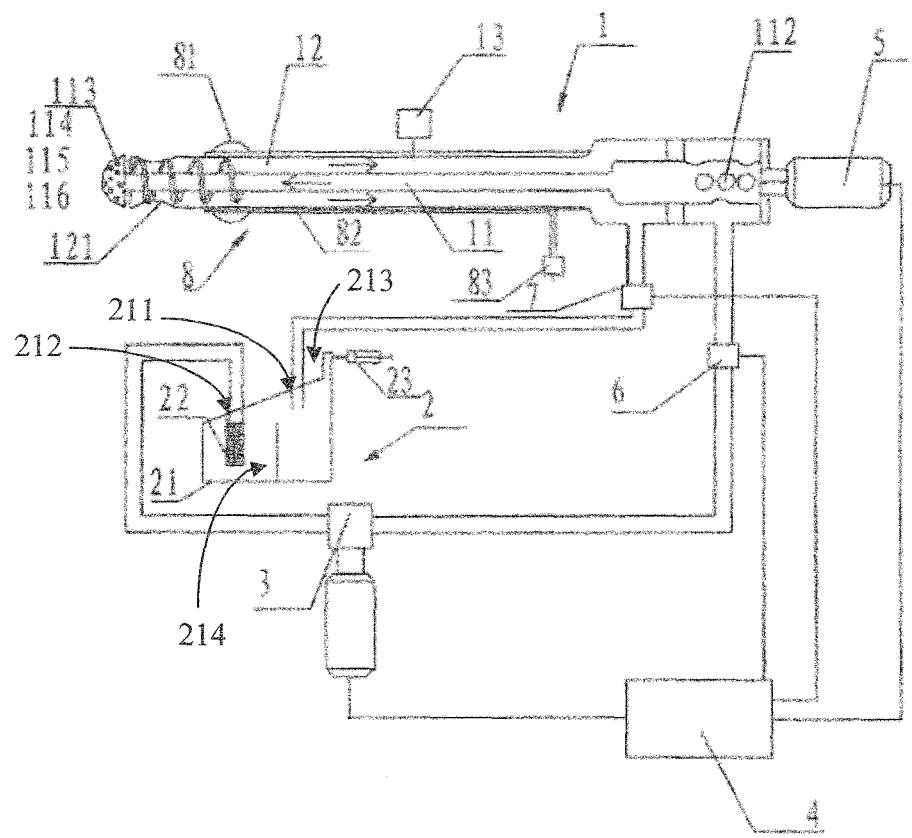
FIG. 3 shows a structure diagram of a hematoma evacuator based on the fluid-storing, filtering, and gas-discharging apparatus in the example two of the present invention.

The hematoma evacuator based on the fluid-storing, filtering, and gas-discharging apparatus of the present invention can also be used to perform the hematoma clearance operation when there is, for example, hematoma in a patient's bladder in the clinical practice. As shown in FIG. 3, the gasbag fixture 8 comprising a gasbag 81, an inflation pipe 82, and an inflation valve 83 is sleeved on the outer wall of the stator 12 based on the structure of the above Embodiment 1; the gasbag fixture 8 is arranged on the aspirator because it is not easy to fix an aspirator when operating on the bladder. Gas or fluid is injected via the inflation valve 83 after the aspirator 1 was put into bladder in the process of the operation. The gasbag 81 is inflated via the inflation pipe 82, so that the aspirator can be fixed by the gasbag and perform the clearing operation. The process of the operation will not be described here as it is the same with the process in the Embodiment 1. The aspirator can be made into flexible structure for adapting the body cavities.

It is thus obvious that the hematoma evacuator of the present invention can not only be used to perform the intracranial hematoma clearance operation, but also be used to clear hematomas and abscesses in other parts of the body, such as hematoma in bladder so that the present invention is able to achieve multiple purposes.

The descriptions mentioned above are only the preferred examples of the present invention, but are not other forms of restrictions for the present invention, and any one of those who skilled in the technique can change or modify them to equivalently changed equivalent examples using the technical content disclosure above. However, any simple modifications, equivalent changes, and remodels made for the above examples according to the technical essence of the present invention and including within the content of the technical solution of the present invention are still within the scope of the technical solutions protection of the present invention.

What is claimed is:

1. A fluid-storing, filtering, and gas-discharging apparatus for hematoma evacuator, wherein the apparatus comprises a fluid holder, a gas detector, and a filter; wherein the fluid holder has a protruding apex and comprises a fluid inlet positioned at the fluid holder and a fluid outlet positioned at an upper part of the fluid holder; a gas-discharging pipe arranged on the protruding apex of the fluid holder to communicate with outside of the fluid holder; wherein the gas detector is arranged on the gas-discharging pipe; wherein the filter is longitudinally set up and is fixed within the fluid holder and is connected to the fluid outlet.

2. The fluid-storing, filtering, and gas-discharging apparatus according to claim 1, further comprising a baffle plate arranged on a lower part of the fluid holder to divide the fluid holder into two fluid chambers, wherein upper parts of the two fluid chambers are connected; wherein the fluid inlet is arranged at a top of the first fluid chamber; wherein the filter is arranged in the second fluid chamber.

3. The fluid-storing, filtering, and gas-discharging apparatus according to claim 1, wherein a lower part of the fluid holder has a convex polyhedron structure.

4. The fluid-storing, filtering, and gas-discharging apparatus according to claim 1, wherein the upper part of the fluid holder has a tapered structure to form the protruding apex.

5. A hematoma evacuator, comprising:
an electrical control unit;
an aspirator configured with a rotor and a stator;
a fluid-storing, filtering, and gas-discharging apparatus;
a circulating pump; and
a rotating device connected to the aspirator respectively, wherein the fluid-storing, filtering, and gas-discharging apparatus comprises a fluid holder, a gas detector, and a filter; wherein the fluid holder has a protruding apex and comprises a fluid inlet positioned at the fluid holder and a fluid outlet positioned at an upper part of the fluid holder; a gas-discharging pipe arranged on the protruding apex of the fluid holder to communicate with outside of the fluid holder; wherein the gas detector is arranged on the gas-discharging pipe; wherein the filter is longitudinally set up and is fixed within the fluid holder and is connected to the fluid outlet; wherein the aspirator is connected to the fluid inlet of the fluid-storing, filtering, and gas-discharging apparatus; wherein the fluid outlet of the fluid-storing, filtering, and gas-discharging apparatus is connected to the circulating pump; wherein the circulating pump is connected to the aspirator to form a closed-loop pathway; wherein the circulating pump and the rotating device are both controlled by the electrical control unit.

6. A hematoma evacuator according to claim 5, further comprising a plurality of connecting pipes and a plurality of pressure sensors arranged on both the connecting pipes between the fluid-storing, filtering, and gas-discharging apparatus and an internal cavity of the stator of the aspirator and between the circulating pump and an internal cavity of the rotor of the aspirator and controlled by the electrical control unit.

7. A hematoma evacuator according to claim 5, further comprising a gasbag fixture sleeved on an outer wall of the stator, and the gasbag fixture comprises a gasbag, an inflation pipe, and an inflation valve for inflating air into the gasbag via the inflation pipe.

* * * * *